(12) United States Patent
Charles (10) Patent No.: US 11,617,682 B2
(45) Date of Patent: Apr. 4, 2023

(54) SURGICAL FOOT PEDAL DEVICE HAVING FORCE FEEDBACK

(71) Applicant: Alcon Inc., Fribourg (CH)

(72) Inventor: Steven T. Charles, Memphis, TN (US)

(73) Assignee: Alcon Inc., Fribourg (CH)

(*) Notice: Subject to any disclaimer, the term of this patent is extended or adjusted under 35 U.S.C. 154(b) by 999 days.

(21) Appl. No.: 16/408,522

(22) Filed: May 10, 2019

(65) Prior Publication Data

US 2019/0350757 A1 Nov. 21, 2019

Related U.S. Application Data

(60) Provisional application No. 62/673,164, filed on May 18, 2018.

(51) Int. Cl.
| | |
|---|---|
| *A61F 9/007* | (2006.01) |
| *A61F 9/008* | (2006.01) |
| *G05G 1/30* | (2008.04) |
| *A61B 17/00* | (2006.01) |

(52) U.S. Cl.
CPC .......... *A61F 9/00745* (2013.01); *A61F 9/008* (2013.01); *A61B 2017/00977* (2013.01); *A61M 2210/0612* (2013.01); *G05G 1/305* (2013.01)

(58) Field of Classification Search
CPC ........... A61B 2017/00017; A61B 2017/00119; A61B 2017/00123; A61B 2017/00398; A61B 2017/00977; A61B 2505/05; A61B 2562/0247; A61B 3/102; A61B 5/0053; A61B 5/03; A61B 5/7455; A61F 9/00736; A61F 9/00745; A61F 9/008; A61M 2210/0612; G05G 1/30; G05G 1/305; G06F 3/0334
See application file for complete search history.

(56) References Cited

U.S. PATENT DOCUMENTS

| | | | |
|---|---|---|---|
| 6,962,581 B2 | 11/2005 | Thoe | |
| 7,781,941 B2 | 8/2010 | Horvath | |
| 8,048,094 B2 | 11/2011 | Finlay | |
| 9,240,110 B2 | 1/2016 | Roth | |
| 10,243,557 B2 | 3/2019 | Ekvall | |
| 10,537,472 B2 | 1/2020 | Brennan | |
| 2012/0302941 A1 | 11/2012 | Teodorescu | |
| 2017/0333253 A1 | 11/2017 | Heeren | |
| 2018/0132948 A1 | 5/2018 | Mercado | |
| 2019/0125182 A1 | 5/2019 | Charles | |

(Continued)

*Primary Examiner* — Brandy S Lee
(74) *Attorney, Agent, or Firm* — Patterson + Sheridan, LLP (57) ABSTRACT

A foot pedal device configured to provide force feedback to an operator during ophthalmic surgery is described. The foot pedal device includes a processor and a memory containing instructions which, when executed by the processor, cause the processor to transmit, in response to a movement of a moveable member, a control signal to a surgical console for initiating an action of an ophthalmic surgery tool coupled with the surgical console. The foot pedal device includes a force feedback mechanism configured to selectively apply a resistance force in opposition to the movement of the movable member. The memory contains instructions which, when executed by the processor, cause the processor to receive, from the surgical console, a trigger signal, and send a force feedback signal to the force feedback mechanism. The force feedback mechanism is configured to apply the resistance force to the movable member upon receiving the force feedback signal.

21 Claims, 4 Drawing Sheets

(56) References Cited

U.S. PATENT DOCUMENTS

| | | |
|---|---|---|
| 2019/0354200 A1 | 11/2019 | Rapoport |
| 2019/0354201 A1 | 11/2019 | Rapoport |
| 2020/0064879 A1 | 2/2020 | Jawidzik |
| 2020/0085515 A1 | 3/2020 | Jawidzik |

SURGICAL FOOT PEDAL DEVICE HAVING FORCE FEEDBACK

BACKGROUND

The present disclosure relates to ophthalmic surgery, and more specifically, to a foot pedal device configured to provide force feedback to an operator, such as an ophthalmic surgeon, during ophthalmic surgery.

In ophthalmology, ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

During ophthalmic surgery, surgeons control actions of various surgery tools. Because surgeons sometimes simultaneously control more than one action of the surgical tools, it is useful to be able to control various actions using foot controls. However, improvements in accuracy and sensitivity of foot controls for ophthalmic surgery remains challenging.

SUMMARY

The present disclosure provides an ophthalmic surgery foot pedal device having force feedback. The ophthalmic surgery foot pedal device includes a housing, a movable member, a movement sensor configured to register a movement of the movable member, a processor, a non-transitory computer-readable medium, a force feedback mechanism configured to selectively apply a resistance force in opposition to a depression of the movable member, and a power supply configured to provide electrical power to the foot pedal device. The non-transitory computer-readable medium contains a first set of instructions which, when executed by the processor, cause the processor to receive a movement signal from the movement sensor, indicating movement of the movable member. The non-transitory computer-readable medium contains a second set of instructions which, when executed by the processor, cause the processor to transmit, in response to the movement signal, a control signal to a surgical console, wherein the ophthalmic surgical tool is configured to perform a controllable action that is actuated in response to the control signal. The non-transitory computer-readable medium also contains a third set of instructions which, when executed by the processor, cause the processor to receive, from the surgical console, a trigger signal indicating a present selectable value of an ophthalmic surgical parameter, and send, in response to the trigger signal, a force feedback signal to the force feedback mechanism. The force feedback mechanism applies a resistance force to the movable member upon receiving the force feedback signal.

A method of operation of the foot pedal device during ophthalmic surgery is also described. The method includes: depressing the movable member, thereby causing movement of the movable member; executing, by the processor, a first set of instructions contained in the non-transitory computer-readable medium, causing the processor to receive an angular position signal indicating an angular position of the foot pedal and/or a movement signal from the movement sensor indicating movement of the movable member; executing, by the processor, a second set of instructions contained in the non-transitory computer-readable medium, in response to the angular position signal and/or the movement signal, causing the processor to transmit a control signal to a surgical console for initiating an actuation of an ophthalmic surgery tool coupled with the surgical console, wherein the ophthalmic surgical tool is configured to perform a controllable action that is actuated in response to a control signal; executing, by the processor, a third set of instructions contained in the non-transitory computer-readable medium, causing the processor to: receive a trigger signal from the surgical console, wherein the trigger signal indicates a present selectable value of an ophthalmic surgical parameter; and send a force feedback signal to the force feedback mechanism, in response to the trigger signal; and applying, by the force feedback mechanism, a resistance force to the movable member, upon receiving the force feedback signal.

In any of the disclosed implementations, the foot pedal device may further include the following details:

i) the trigger signal may be a stopping signal, indicating that the present selectable value of an ophthalmic surgery parameter is selected from a) a value equal to or greater than a selectable maximum threshold value of the ophthalmic surgery parameter, and b) a value equal to or less than a minimum threshold value of the ophthalmic surgery parameter, and the resistance force is a stopping force that prevents depression of the movable member;

ii) the trigger signal may be a slowing signal, and the resistance force is a slowing force providing resistance to depression of the movable member, wherein the resistance does not prevent depression of the movable member;

iii) the slowing signal may indicate a present value of a surgical parameter that is selected from a) between a maximum threshold value of the surgical parameter and a value at a set difference lower than the maximum threshold value of the surgical parameter, or b) between a minimum threshold value of the surgical parameter and a value at a set difference higher than the minimum threshold value of the surgical parameter;

iv) the slowing signal may indicate a selectable present value that is a product of present values of two or more ophthalmic surgery parameters;

v) at least one of the ophthalmic surgery parameters may be a parameter of the controllable action of the ophthalmic surgery tool;

vi) the slowing signal may indicate that a present value of the parameter of the controllable action is a non-optimal value, wherein the non-transitory computer-readable medium further contains a lookup table containing a range of optimal values of the controllable action of a surgical tool in view of the two or more ophthalmic surgery parameters; the processor, upon execution of a fourth set of instructions contained in the non-transitory computer readable medium, is configured to compare the present value of a parameter of the controllable action of the surgical tool in view of the present values of the two or more ophthalmic surgery parameters with the optimal value contained in the lookup table in view of the present values of the two or more ophthalmic surgery parameters; and determine that the present value of the parameter of the controllable action of the surgical tool is different to the optimal value of the parameter of the controllable action of the surgical tool;

vii) the surgical parameter may be detectable by one or more surgical sensors coupled with the surgical console;

viii) the surgical parameter sensor may be configured to detect an ophthalmic surgery parameter selected from one of fluidics resistance, lens hardness, intra-ocular pressure, vacuum, irrigation pressure, irrigation valve speed, vent valve direction, vent speed, pump direction, pump speed, fluidics fluid level, infusion pressure, vitrectomy cutter cuts per minute (CPM), and laser power;

ix) the ophthalmic surgery tool may be selected from one of a flow pump, a vacuum pump, a phacoemulsification tool, a vitrectomy probe, a laser probe, a syringe configured as a power injector or extraction device, and an OCT imaging tool;

x) the controllable action may be selected from one of stroke length, cutting speed, vacuum level, aspiration flow rate, irrigation valve speed, vent valve direction, vent speed, pump direction, pump speed, fluidics fluid level, infusion pressure, vitrectomy cutter cuts per minute (CPM), laser power, and syringe plunger depression;

xi) the force feedback mechanism may include at least one of a torque motor, a brushless torque motor, brushless slotless DC motor, a frictional brake, an electromagnetic brake, and a pumping brake;

xii) the ophthalmic surgery foot pedal device may include a depression force sensor configured to detect a depression force applied to the movable member, wherein the non-transitory computer-readable medium contains a fifth set of instructions which, when executed by the processor, cause the processor to receive, from the depression force sensor, a first depression force value; receive, from the depression force sensor, a modified depression force value in response to the slowing force; make a determination that the modified depression force value is a threshold percentage higher than the first depression force value; and in response to the determination, transmit a control signal to the surgical console;

xiii) the ophthalmic surgery foot pedal device may include a depression force sensor configured to detect a depression force applied to the movable member, wherein the non-transitory computer-readable medium contains a sixth set of instructions which, when executed by the processor, cause the processor to receive, from the depression force sensor, a first depression force value; receive, from the depression force sensor, a modified depression force value in response to the slowing force; make a determination that the modified depression force value is a threshold percentage lower than the first depression force value; and in response to the determination, cause the force feedback mechanism to end the application of the slowing force;

xiv) the threshold difference may be calibrated for a selected operator;

xv) the threshold difference calibrated for a selected operator may include recording a set of calibration depression force values for the selected operator, including the steps of a) performing a first foot depression to the movable member coincident with an initiation of a slowing force, wherein the first foot depression has a first depression force value, b) recording the first depression force value to the non-transitory computer-readable medium, c) performing a second foot depression to the movable member, wherein the second foot depression is a modified foot depression intentionally applied to the movable member in response to the slowing force to further depress the movable member, and the modified foot depression has a modified depression force value that is a threshold difference higher than the first depression force value, and d) recording the modified depression force value to the non-transitory computer-readable medium;

xvi) the threshold difference calibrated for a selected operator may include recording a set of calibration depression force values for the selected operator, including the steps of a) performing a first foot depression to the movable member coincident with an initiation of a slowing force, wherein the first foot depression has a first depression force value, b) recording the first depression force value to the non-transitory computer-readable medium, c) performing a second foot depression to the movable member, wherein the second foot depression is a modified foot depression applied to intentionally decrease or cease the depression force applied to the movable member in response to the slowing force, and the modified foot depression has a modified depression force value that is a threshold difference lower than the first depression force value, and d) recording the modified depression force value to the non-transitory computer-readable medium;

xvii) the power supply may further include a wireless charging system;

xviii) the force feedback mechanism may include a brushless torque motor;

xix) the method may further include executing, by the processor, a fifth set of instructions contained in the non-transitory computer-readable medium, causing the processor to: receive a first depression force value signal from the depression force sensor; receive a modified depression force value signal in response to the slowing force; make a determination that the modified depression force value is a threshold difference higher than the first depression force value; and transmit a control signal to the surgical console in response to the determination.

While a depression force sensor is described extensively, those with ordinary skill in the art having the benefit of the present disclosure will readily appreciate that a wide variety of sensors can be used to detect movement, rotation, position, depression, force, etc. imparted onto the movable member of a foot pedal. In some cases, the foot pedal utilizes an angular position sensor (such as a Hall effect or optical encoder) to provide a signal to the console with the signal conveying a value proportional to foot pedal depression angle. Likewise, a modified depression angle in response to a slowing force can be used to transmit a further control signal to the console.

BRIEF DESCRIPTION OF THE DRAWINGS

For a more complete understanding of the present disclosure, reference is now made to the following description, taken in conjunction with the accompanying drawings, in which.

DETAILED DESCRIPTION

In the following description, details are set forth by way of example to facilitate discussion of the disclosed subject matter. It should be apparent to a person of ordinary skill in the art, however, that the disclosed implementations are exemplary and not exhaustive of all possible implementations.

The present disclosure relates to ophthalmic surgery, and more specifically, to a foot pedal device configured to provide force feedback to an operator, such as an ophthalmic surgeon, during ophthalmic surgery.

Ophthalmic surgery is performed on the eye and accessory visual structures. For example, vitreoretinal surgery encompasses various delicate procedures involving internal portions of the eye, such as the vitreous humor and the retina.

Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

Ophthalmic surgery often involves removal of eye tissue. For example, cataract surgery generally requires the removal and replacement of the lens. An artificial lens or intraocular lens implant can then be implanted within the eye to restore or improve the eyesight of the patient. Other procedures may also involve the removal of lens tissue and/or other types of eye tissue.

There are a number of procedures and devices that have been developed for the removal of eye tissue. For example, phacoemulsification is a widely used method for removal of diseased or damaged lens tissue. The phacoemulsification process generally involves insertion of a probe through a small corneal incision to break apart and remove the lens in cataract surgery.

In phacoemulsification, one or more incisions are generally made in the eye to allow the introduction of surgical instruments. The surgeon then removes the anterior face of the capsule that contains the lens inside the eye. An ultrasonic handpiece, where the tip vibrates at ultrasonic frequency, is generally used to sculpt and emulsify the cataract. After removal of the cataract, the posterior capsule is generally still intact and an intraocular lens implant (IOL) can be placed into the remaining lens capsule.

Given the need for fine-tuned control during ophthalmic surgery, improvements in equipment used by an ophthalmic surgeon to provide the operator with increased control over surgical techniques is expected to improve surgical outcomes for the patient. Foot pedals can be used for control of various surgery tools during ophthalmic surgery. Accordingly, improvements in foot pedals used in ophthalmic surgery to allow the operator to have more control over various surgical procedures is desirable. In particular, improvements in integration of foot pedal control with surgical consoles, including surgical tools and sensors configured to detect parameters related to ophthalmic surgery, and the ability to provide the operator with advanced force feedback through the foot pedal would provide the operator with increased awareness of present conditions related to the surgery and the ability to execute more fine-tuned control of the surgery.

The present disclosure generally relates to the use of haptic communication to provide a force feedback through a foot pedal device to an operator during ophthalmic surgery.

In general, it is understood that the term "haptic communication" refers to the communication of information to the operator by applying mechanical stimulation such as forces, vibrations, or motions to a body part of the operator that can be detected by the operator through the sense of touch. The mechanical stimulation can be used to enhance an ability of the operator to control machines and devices that incorporate haptic communication. The machines or devices may also incorporate sensors that measure forces exerted by the operator on the machine or device or angular position input. While a depression force sensor is described extensively, those with ordinary skill in the art having the benefit of the present disclosure will readily appreciate that a wide variety of sensors can be used to detect movement, rotation, position, depression, force, etc. imparted onto the movable member of a foot pedal. In some cases, the foot pedal utilizes an angular position sensor (such as a Hall effect or optical encoder) to provide a signal to the console with the signal conveying a value proportional to foot pedal depression angle. Likewise, a modified depression angle in response to a slowing force can be used to transmit a further control signal to the console.

In particular, the term "force feedback", as used herein in relation to a foot pedal device, refers to a force providing a controllable resistance force in opposition to a depression and/or angular position rotation of a movable member of a foot pedal device. The term "controllable resistance force" refers to a type of active force feedback that is able to be controlled, such as the ability to turn the resistance force on, off, or increase or decrease the amount of resistance force in opposition to depression of the movable member. In particular, control of the force feedback can be executed by a computer processor executing instructions contained within a non-transitory computer-readable medium, as described herein.

In addition to the controllable resistance force provided by the force feedback mechanism described herein, the foot pedal device may also include a passive resistance mechanism, such as a spring return to provide a minimal resistance configured for passively rotating the movable member towards an open position in absence of any depression force on the movable member.

The term "open position" as used herein refers to a terminally raised position of the movable member, such as the position of the movable member in absence of any depression force and/or angular rotation. In contrast, the term "closed position" as used herein refers to a terminally lowered position of the movable member, such as the position of the movable member wherein the movable member is fully depressed and/or angularly rotated.

Figure 1A:
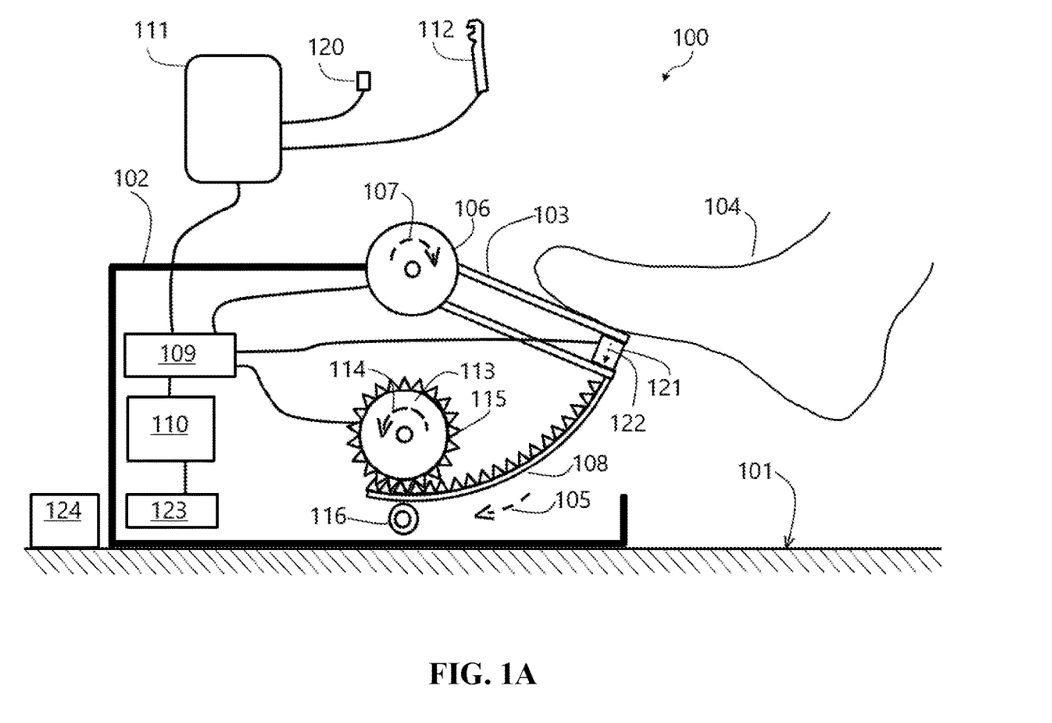
FIG. 1A shows a schematic diagram (not drawn to scale) of an exemplary ophthalmic surgery foot pedal device.
Figure 1B:
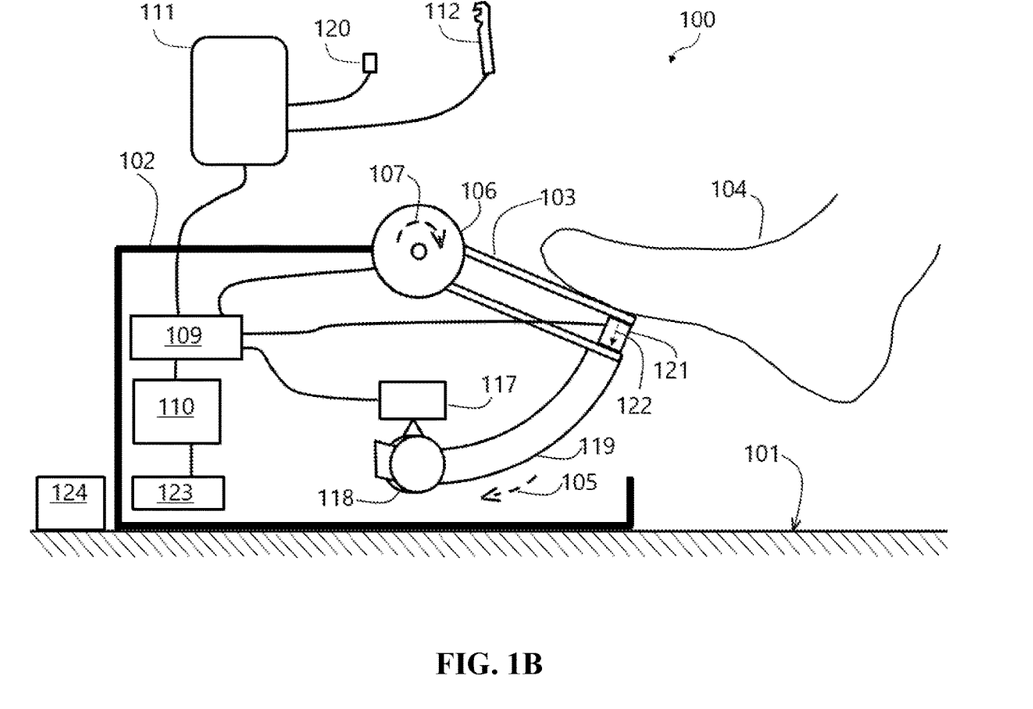
FIG. 1B shows another schematic diagram (not drawn to scale) of an exemplary ophthalmic surgery foot pedal device.

FIG. 1A and FIG. 1B show exemplary schematic diagrams of a foot pedal device 100. It is to be understood that the foot pedal device 100 shown in FIG. 1A and FIG. 1B is exemplary and non-limiting, and that other configurations of the foot pedal device that are operative within the scope of the present disclosure are identifiable by persons skilled in the art. Modifications, additions, or omissions may be made to the ophthalmic surgery foot pedal device 100 without departing from the scope of the disclosure. The components and elements of the ophthalmic surgery foot pedal device 100, as described herein, may be integrated or separated according to particular applications. The ophthalmic surgery foot pedal device 100 may be implemented using more, fewer, or different components in some implementations.

FIG. 1A depicts an exemplary ophthalmic surgery foot pedal device 100. FIG. 1A is a schematic diagram and is not drawn to scale or perspective. In FIG. 1A, the ophthalmic surgery foot pedal device 100 is shown resting on a surface 101, such as the floor or the ground, during operation. The exemplary ophthalmic surgery foot pedal device has a housing 102 and a movable member 103 connected to, contained in or otherwise attached, directly or indirectly, to the housing. As shown in FIG. 1A, the movable member of the exemplary ophthalmic surgery foot pedal device 100 is configured so that depression of the movable member 103 by a foot 104 of an operator causes the movable member 103 to partially rotate through an arc from an open position to a closed position, depicted by a dashed clockwise curved arrow 105 in FIG. 1A. The foot pedal device 100 has a movement sensor 106 configured to register a movement of the movable member 103. Any mechanical and/or electronic components identifiable by skilled persons operable to register movement of the movable member, such as a rotary encoder, can be used in the ophthalmic surgery foot pedal device of the present disclosure. The term "rotary encoder", also called a shaft encoder, refers to an electro-mechanical device that converts angular position or motion to an electronic signal. As shown in FIG. 1A, the exemplary movement sensor 106 is a rotary encoder rotatably connected to the movable member 103, as depicted by a dashed clockwise arrow 107. The movable member 103 can also include an extended portion 108, which can be configured to interface with a force feedback mechanism, as described herein.

The ophthalmic surgery foot pedal device 100 includes a processor 109 and a non-transitory computer-readable medium 110, also referred to herein as "memory". Any suitable processor identifiable by skilled persons can be used in the ophthalmic surgery foot pedal device 100. For example, the processor 109 may real time operating system or another suitable operating system. The non-transitory computer-readable medium 110 can encompass persistent and volatile media, fixed and removable media, and magnetic and semiconductor media, among others identifiable by persons of ordinary skill in the art. In addition, any suitable communication interface identifiable by skilled persons can be used for transmittal and receipt of electronic communication signals between the components of the ophthalmic surgery foot pedal device 100 described herein.

The non-transitory computer-readable medium 110 contains a first set of instructions which, when executed by the processor 109, cause the processor to receive a movement signal from the movement sensor 106, indicating movement and/or angular position of the movable member 103, and thereby detects a movement and/or change in the angular position of the movable member 103. The non-transitory computer-readable medium 110 contains a second set of instructions which, when executed by the processor 109, cause the processor 109 to transmit, in response to the movement and/or change in angular position of the moveable member 103, a control signal to a surgical console 111 for initiating an actuation of a controllable action of an ophthalmic surgery tool 112 coupled with the surgical console 111. In response to the movement signal, the surgical console 111 is configured to transmit a control signal to the ophthalmic surgery tool 112.

The foot pedal device 100 may be used to control the actuation of any ophthalmic surgery tool 112 that is configured to perform a controllable action that is actuated in response to a control signal. Examples of such ophthalmic surgery tools include phacoemulsification tools, vitrectomy probes, laser probes (e.g., for pan retinal photocoagulation), among others identifiable by skilled persons upon reading the present disclosure, such as flow pumps, vacuum pumps, aspirators, cutters, syringes, and others. The foot pedal device 100 can be configured to control actions of ophthalmic surgery tools 112 used in complex surgical procedures such as phacoemulsification, and also simpler surgical procedures, such as depression of a syringe plunger. The foot pedal device 100 can be configured to control a single ophthalmic surgical tool 112, or a plurality of ophthalmic surgical tools 112, wherein each of the ophthalmic surgical tools 112 can be independently controlled by a selectable control signal selected from a plurality of control signals whereby the processor 109 is configured to execute a selectable second set of instructions contained in the non-transitory computer-readable medium. The foot pedal device 100 may also be operatively connected to a computer interface and/or display (not shown) whereby the operator can select which ophthalmic surgical tool 112 and/or which controllable action of an ophthalmic surgical tool 112 is controlled by the foot pedal device 100.

The term "controllable action of an ophthalmic surgical tool" as used herein refers to any controllable function that can be actuated upon receipt of a control signal, performed by an ophthalmic surgery tool 112 such as the tools described herein and others identifiable by those skilled in the art. In general, the foot pedal device 100 can be configured to control any action of an ophthalmic surgical tool 112 that is controllable by the surgical console 111. Examples of controllable actions of ophthalmic surgery tools include increasing stroke length (thereby increasing ultrasonic power) of a probe, increasing cutting speed of vitrectomy cutter, controlling intraocular pressure (TOP), vacuum power, aspiration power, and any other settings controllable by the surgical console 111. The foot pedal device 100 can also control actions of tools for techniques such as imaging, such as control of scrolling through layers of an optical coherence tomography (OCT) image.

The term "surgical console" as used herein refers to an apparatus or system configured to be used by an operator, such as an ophthalmic surgeon, to perform one or more ophthalmic surgery techniques, and may include various components such as surgical tools, instruments, sensors, hardware, software, computers, lighting, power supply, cameras, pumps, solutions, and imaging systems, among other components identifiable by persons skilled in the art. Exemplary surgical consoles include the CONSTELLATION® console and the CENTURION® console (both sold by Alcon Vision, LLC), among others identifiable by skilled persons.

The ophthalmic surgery foot pedal device 100 also has a force feedback mechanism configured to selectively apply a resistance force in opposition to the depression of the movable member towards the closed position. The force feedback mechanism of the foot pedal device 100 is not configured to rotate the movable member towards the open position, but instead is configured to apply a resistance force that increases the depression force required to depress the movable member towards the closed position. The force feedback mechanism can be configured to apply a resistance force to varying degrees, including a complete locking of the force feedback mechanism, effecting a full stop of the movement of the movable member, or a partial resistance force effecting a resistance to depression of the movable member that does not cause the movable member to completely stop, as described herein.

FIG. 1A shows, in schematic form, an exemplary force feedback mechanism that includes a torque motor 113 configured to apply a rotational force (depicted in FIG. 1A as a counter-clockwise curved dashed arrow 114) to the movable member opposition to the rotation towards the closed position of the movable member 103.

As depicted in schematic form, the exemplary force feedback mechanism shown in FIG. 1A includes a torque motor 113 having an actuator 115, schematically depicted in FIG. 1A as a gear having teeth, that is rotatably connected to the torque motor 113, that is schematically depicted as interfacing with an extended portion 108 of the movable member having gear teeth rotatably interconnected with the gear teeth of the actuator 115. Also shown is a guide wheel 116 situated below the extended portion 108 of the movable member to assist in maintaining the rotatable connection of the actuator 115 with the extended portion 108 of the movable member. As would be understood by skilled persons, the term "torque motor" refers to a specialized form of electric motor which can operate indefinitely while stalled, that is, with the rotor blocked from turning, without incurring damage. In this mode of operation, the motor will apply a steady torque to a load, such as the load produced from a depression force on the movable member 103 of the ophthalmic surgery foot pedal device 100.

In particular, the torque motor may be a brushless torque motor. The term "brushless torque motor" as used herein typically refers to a brushless DC electric motor, also known as an electronically commutated motor, or a synchronous DC motor, which are synchronous motors powered by DC electricity via an inverter or switching power supply which is configured to produce an AC electric current to drive each phase of the motor via a closed loop controller. In a brushless DC electric motor, the controller is typically configured to provide pulses of current to the motor windings that control the speed and torque of the motor.

As would be understood by persons of ordinary skill in the art, an electric motor typically develops torque by magnetic force between rotating magnets on a rotor, the turning part of the machine, and stationary magnets on a stator which surrounds the rotor. One or both sets of magnets may be electromagnets, typically made of a coil of wire wound around an iron core. Electric current through the wire winding creates the magnetic field, providing the power which runs the motor. Each time the rotor rotates by 180° (a half-turn), the position of the north and south poles on the rotor are reversed. In brushed motors, this is done with a rotary switch on the motor's shaft called a commutator. It consists of a rotating cylinder divided into multiple metal contact segments on the rotor. The segments are connected to wire electromagnet windings on the rotor. Two or more stationary contacts called "brushes", made of a soft conductor like graphite press against the commutator, making sliding electrical contact with successive segments as the rotor turns, providing electric current to the windings. Each time the rotor rotates by 180° the commutator reverses the direction of the electric current applied to a given winding, so the magnetic field creates a torque in one direction. In contrast, in a brushless motor, an electronic servo system replaces the mechanical commutator contacts. Typically, an electronic sensor detects the angle of the rotor, and controls semiconductor switches such as transistors which switch current through the windings, either reversing the direction of the current, or in some motors turning it off, at the correct time each 180° shaft rotation so the electromagnets create a torque in one direction. A typical brushless motor has permanent magnets which rotate around a fixed armature. An electronic controller replaces the brush/commutator assembly of the brushed DC motor, which continually switches the phase to the windings to keep the motor turning. The controller can perform similar timed power distribution by using a solid-state circuit rather than the brush/commutator system. Brushless motor commutation can be implemented in software using a microcontroller or microprocessor computer, or may alternatively be implemented in analogue hardware, or in digital firmware, such as using a field programmable gate array. Controller implementations for detecting the rotor's orientation/position (relative to the stator coils) may include designs that use Hall effect sensors, or a rotary encoder to directly measure the rotor's position, or others that measure the back-EMF in the undriven coils to infer the rotor position, among others identifiable by skilled persons. Brushless motors can be constructed in several different physical configurations: in the "conventional" (also known as "in-runner") configuration, the permanent magnets are part of the rotor. Three stator windings typically surround the rotor. In the "out-runner" (or external-rotor) configuration, the radial-relationship between the coils and magnets is reversed; the stator coils form the center (core) of the motor, while the permanent magnets spin within an overhanging rotor which surrounds the core. Alternatively, a flat or axial flux type, typically used where there are space or shape limitations, uses stator and rotor plates, mounted face to face. There are two common electrical winding configurations; the delta configuration connects three windings to each other (series circuits) in a triangle-like circuit, and power is applied at each of the connections. The Wye (Y-shaped) configuration, sometimes called a star winding, connects all of the windings to a central point (parallel circuits) and power is applied to the remaining end of each winding. Brushless torque motors are commercially available from vendors such as Moog Inc., Aerotech Inc., Maxon Precision Motors, Inc., Allied Motion Technologies, Inc., and B. Ketterer Sohne GmbH & Co. KG, among others.

Any suitable force feedback mechanism identifiable by persons skilled in the art can be used in the ophthalmic surgery foot pedal device 100. Other force feedback mechanisms that can be used in the foot pedal device 100 include frictional brakes, electromagnetic brakes and pumping brakes, among others identifiable by skilled persons upon reading the present disclosure.

The term "frictional brake" as used herein refers to a mechanism configured to use friction generated when a first surface of a moving object and a second surface of a stationary object are pressed together to convert the kinetic energy of the moving object into heat. As depicted in schematic form in FIG. 1B, another exemplary force feedback mechanism includes a frictional brake having a brake caliper 117 that, when activated by the force feedback signal from the processor 109, initiates movement of a pair of brake pads 118 together to press against both sides of the extended portion of the movable member that forms a partial disc 119, thereby using friction to cause force feedback against the depression of the movable member 103, selectively causing it to slow or stop, similar to the typical action of brake pads applying braking force on a disc in a braking mechanism in an automobile. In the exemplary force feedback mechanism, upon receiving the force feedback signal, the caliper 117 can be configured to force the brake pads 118 against both sides of the partial disc 119 using mechanical, hydraulic, pneumatic or electromagnetic means, among other mechanisms identifiable by skilled persons. Other configurations of frictional brakes operable within the scope of the disclosure are identifiable by skilled persons, such as those having a single brake pad, or having a drum brake instead of a disc brake, and so on.

The term "electromagnetic brake" as used herein can refer to an "electro-mechanical brake", which is a type of frictional brake that can use magnetic attraction between the brake pads and the 'disc', or the extended portion of the movable member, to initiate friction braking. In some configurations of the foot pedal device, the term "electromagnetic brake" can also refer to a brake configured as an electric motor generator, wherein the generated electricity can then be sent to a resistor bank and dumped as heat, or a generator with an internal short-circuit that functions as a "retarder" brake, as would be understood by skilled persons.

Alternatively, in other configurations of the foot pedal device, an electromagnetic brake can be configured to initiate braking through electromagnetic induction, which creates resistance and in turn either heat or electricity. Related types of electromagnetic brakes are referred to as "eddy current brakes", unlike friction brakes, in which the drag force that stops the moving object is provided by friction between two surfaces pressed together, the resistance force, or drag force in an eddy current brake is an electromagnetic force between a magnet and a nearby conductive object in relative motion, due to eddy currents induced in the conductor through electromagnetic induction. A conductive surface moving past a stationary magnet will have circular electric currents called eddy currents induced in it by the magnetic field, as described by Faraday's law of induction. By Lenz's law, the circulating currents will create their own magnetic field which opposes the field of the magnet. Thus, the moving conductor will experience a drag force from the magnet that opposes its motion, proportional to its velocity. The kinetic energy of the moving object is dissipated as heat generated by the current flowing through the electrical resistance of the conductor. In an eddy current brake, the magnetic field may be created by a permanent magnet, or an electromagnet so the braking force can be turned on and off or varied by varying the electric current in the electromagnet's windings.

In some configurations of the foot pedal device, a force feedback mechanism such as an electromagnetic braking mechanism or other mechanism, can incorporate the use of a flywheel that rotates in response to the depression of the movable member, and a frictional or electromagnetic force applied against the movement of the flywheel can provide a resistance force, as would be understood by skilled persons.

The term "pumping brake" as used herein refers to a brake configured to force a fluid, such as a liquid or a gas through a cylinder. For example, the liquid can be an oil, and the gas can be compressed air. An exemplary configuration of a foot pedal device includes a pumping brake mechanism that forces a fluid through a portal from a first compartment to a second compartment upon depression of the movable member. Upon receiving the force feedback signal, the size of the portal can be constricted to provide resistance to the movement of the fluid from the first compartment to the second compartment. Alternatively, the portal can be completely closed, to lock the force feedback mechanism, thereby stopping the depression of the movable member.

The non-transitory computer-readable medium 110 contains a third set of instructions which, when executed by the processor 109, cause the processor 109 to receive, from the surgery console 111, a trigger signal, indicating a present selectable value of an ophthalmic surgical parameter, and send, in response to the trigger signal, a force feedback signal to the force feedback mechanism. The force feedback mechanism applies the resistance force to the movable member upon receiving the force feedback signal.

In operation of the ophthalmic surgery foot pedal device described herein, the force feedback can be given in response to a wide variety of ophthalmic surgical parameters. The term "surgical parameter" as used herein refers to any quantitatively measurable factor that is related to ophthalmic surgery, and that establishes a measurable condition under which the ophthalmic surgery is performed. In particular, surgical parameters include a range of values and in particular quantitative measurements of factors such as physical or chemical factors that can be informative for effectively performing ophthalmic surgery.

Exemplary surgical parameters include fluidics resistance, lens hardness, intra-ocular pressure, vacuum, irrigation pressure, irrigation valve speed, vent valve direction, vent speed, pump direction, pump speed, fluidics fluid level, infusion pressure, vitrectomy cutter cuts per minute (CPM), and laser power.

In the foot pedal device, the surgical parameter may be detected by a surgical parameter sensor 120 coupled with surgical console 111. The term "sensor" as used herein refers to a component such as a device or system of devices, typically an electronic device or system, that is configured to detect a range of values of a parameter, indicating a present condition and/or a change in a condition of a parameter in a target environment, and transmit a signal containing information on the parameter values to other electronics, typically a computer processor. Accordingly, the term "surgical parameter sensor" as used herein refers to any component identifiable by skilled persons that is operable to detect a range of values of a surgical parameter indicating a present condition and/or a change in a condition of a parameter in a target environment, wherein the term "target environment" as used herein refers to the internal or external environment of an eye, including the tissues, cells and fluids and other parts of the eye itself, such as lens, retina, vitreous humor, and accessory visual structures, and related fluids such as balanced salt solution (BSS), and in particular is configured to detect parameter values indicating related changes in conditions or events in the target environment during ophthalmic surgery.

The surgical parameter sensor can be separate from, integrated with, or connected to a surgical tool coupled with the surgery console.

The term "intraocular pressure" or "TOP" as used herein refers to the fluid pressure inside the eye. TOP is typically measured with a tonometer and measurement is referred to as tonometry. Most tonometers are calibrated to measure pressure in millimeters of mercury (mmHg). Various types of tonometers and methods of tonometry can be used. Such methods include applanation tonometry, in which the intraocular pressure (IOP) is inferred from the force required to flatten (applanate) a constant area of the cornea. In dynamic contour tonometry (DCT), a tonometry sensor tip contains a hollow the same shape as the cornea with a miniature pressure sensor in its center. Electronic indentation tonometers use a free-floating transducer to detect the transmitted pressure. Rebound tonometers determine intraocular pressure by bouncing a small plastic tipped metal probe against the cornea. The device uses an induction coil to magnetise the probe and fire it against the cornea. As the probe bounces against the cornea and back into the device, it creates an induction current from which the intraocular pressure is calculated. A pneumatonometer utilizes a pneumatic sensor (typically having a piston floating on an air bearing). Filtered air is pumped into the piston and travels through a small (5 mm (0.20 in) diameter) fenestrated membrane at one end. This membrane is placed against the cornea. The balance between the flow of air from the machine and the resistance to flow from the cornea affect the movement of the piston and this movement is used to calculate the intra-ocular pressure. Impression tonometry (also known as indentation tonometry) measures the depth of corneal indentation made by a small plunger carrying a known weight. The higher the intraocular pressure, the harder it is to push against and indent the cornea. Transpalpebral tonometry refers to methods of measuring intraocular pressure through the eyelid. The Diaton non-corneal tonometer calculates pressure by measuring the response of a free-falling rod, as it rebounds against the tarsal plate of the eyelid through the sclera. The patient is positioned so that the tip of the device and lid are overlying sclera. Non-contact tonometry (e.g., air-puff tonometry) uses a rapid air pulse to applanate (flatten) the cornea. Corneal applanation is detected via an electro-optical system. Intraocular pressure is estimated by detecting the force of the air jet at the instance of applanation. The ocular response analyzer (ORA) is a non-contact (air puff) tonometer that provides additional information on the biomechanical properties of the cornea. It uses an air pulse to deform the cornea into a slight concavity. The difference between the pressures at which the cornea flattens inward and outward is measured by the machine and termed corneal hysteresis (CH). The machine uses this value to correct for the effects of the cornea on measurement.

In particular, the range of values of the surgical parameter includes a triggering surgical parameter value. The term "triggering surgical parameter value" as used herein refers to a detected value of the related surgical parameter that triggers the ophthalmic surgery foot pedal device 100 to provide a force feedback to the operator, as described herein. Accordingly, the processor 109, executing a third set of instructions contained in the non-transitory computer-readable medium 110, is configured to receive, from the surgical console 111, a trigger signal indicating a present selectable value of an ophthalmic surgery parameter.

Accordingly, the processor 109 is configured to send, in response to a trigger signal, a force feedback signal to the force feedback mechanism of the ophthalmic surgery foot pedal device 100, wherein the force feedback mechanism is configured to apply a resistance force in opposition to a depression of the movable member 103 upon receiving the force feedback signal. In some implementations, the resistance force may be a stopping force that prevents depression of the movable member. In other implementations, the resistance force may be a slowing force, providing a resistance to depression of the movable member, wherein the resistance does not prevent depression of the movable member.

The trigger signal can be a stopping signal indicating a "stopping value" wherein the present value of an ophthalmic surgery parameter is selected from a) a value equal to or greater than a selectable maximum threshold value of the ophthalmic surgery parameter, and b) a value equal to or less than a minimum threshold value of the ophthalmic surgery parameter.

The term "threshold value of the ophthalmic surgery parameter" as used herein refers to a set minimum or maximum value that can be a pre-determined and/or user-defined value for the parameter. For any given parameter, a minimum and/or maximum value can be set. In particular, the threshold surgical parameter value can be a value indicating a critical condition that should not be passed (either below a minimum value or above a maximum value) during ophthalmic surgery, in particular to avoid conditions during surgery that may cause harm to the patient and/or surgical equipment.

Accordingly, upon detection of a stopping value, the processor can receive a stopping signal from the surgical console. The term "stopping signal" as used herein refers to a signal that initiates application of the stopping force to the movable member, wherein the term "stopping force" refers to a force that prevents depression of the movable member. In this way, the ophthalmic surgery foot pedal device is configured to prevent further depression of the movable member upon detection of a stopping value. Thus, the threshold value of a surgical parameter can provide a range of values, for example above a minimum threshold surgical parameter value and/or below a maximum threshold surgical parameter value, that can allow control of the surgery, so that the transmittal of the control signal to initiate actuation of a controllable action of the ophthalmic surgical tool is restricted to occur within the range of values above a minimum threshold parameter value or below a maximum threshold parameter value, for a given parameter, during the surgery.

For example, during phacoemulsification, one of the goals of the surgery is to maintain a stable anterior chamber of the eye. This can be done by making sure the fluid entering the eye, also referred to as "inflow fluid" is equal to the amount that exits, also referred to as "outflow fluid". This will keep the anterior chamber pressurized. As would be understood by skilled persons, the inflow fluid originates in an irrigation bottle and is a balanced salt solution (BSS). The fluid travels typically from the irrigation bottle through plastic tubing, into a phaco needle and finally into the anterior chamber of the eye. To create a pressure gradient the bottle can be placed at a height above the patient. When a pinch valve is open the fluid in the bottle and tubing creates pressure in the anterior chamber. Approximately 11 mm Hg pressure (above ambient atmospheric pressure) is produced intraocular for every 15 cm (6 inches) bottle height above the patient's eye (Barry S Seibel, Phacodynamics: Mastering the tools and techniques of cataract surgery, third addition, Thorofare, N.J. Slack 1999). The term "outflow" refers to fluid that leaves the anterior chamber. Fluid leaves through the phaco needle into the tubing and into the anterior chamber of the eye. The inflow rate can be increased by increasing the aspiration flow rate. If the balance between inflow and out flow is altered, the anterior chamber can be under-pressurized or over-pressurized. For example, if under pressurized, this can lead to shallowing and/or collapse on the anterior chamber. This can cause forward movement of the iris, lens and posterior capsule. This may lead to inadvertent rupture of the posterior capsule, due to its movement towards the phaco needle. The term "aspiration rate" refers to the amount of fluid flowing through the tubing. This is typically reported in cubic centimeters per minute (cc/min). With a peristaltic pump, flow is determined by the speed of the pump. As flow increases the current in the anterior chamber increases how well particulate matter is attracted to the phaco tip. The "pump" is the part of the surgery console which moves fluid through the aspiration tubing. The pump settings control the rate of movement of the fluid. Pumps used in phacoemulsification surgery consoles include flow pumps and vacuum pumps. Flow pumps include, for example, peristaltic pumps. Flow pumps allow for independent control of both aspiration rate and aspiration level. Vacuum pumps include, for example, venturi pumps. Vacuum pumps allows direct control of only vacuum level, wherein flow is dependent upon the vacuum level setting. The term "vacuum" refers to a negative difference in fluid pressure among two points, typically measured in mm Hg. During phacoemulsification, vacuum determines how well, once occluded on the phaco tip, nuclear material will be held to the tip (also known as 'holding power'). The term "compliance" refers to a change of the tubing shape and volume when put under negative pressure. When the tip of the phaco needle is occluded, vacuum will increase in the tubing. The higher the compliance the more change in the tube's volume. When vacuum is increased, highly compliant tubing collapses on itself reducing its inner volume's capacity. When the occlusion breaks, the tubing returns to its original shape causing a rapid exit of fluid from the anterior chamber, referred to as a "surge". In other words, vacuum can increase when the phaco tip is occluded, and when the occlusion breaks, the rate of fluid exit from the anterior chamber can be temporarily increased due to the sudden expansion of the tubing. This can cause temporary decrease in IOP until the fluid is replaced by the infusion. Selecting lower levels of flow and vacuum, for example, can reduce the amount of surge.

Accordingly, for example, a threshold value of a surgical parameter can be a set maximum vacuum value, or a set minimum IOP value, among others identifiable by skilled persons. Also, upon detection of a present IOP value equal to or less than a set minimum threshold IOP value, or a present vacuum value equal to or greater than a set maximum threshold vacuum value, application of the stopping force can prevent the operator from further depressing the movable member to initiate increased vacuum, which may prevent an occurrence of an occlusion break surge (see, for example, Sharif-Kashkani et al., (2014) BMC Ophthalmology 14:96). Thus, upon receipt of a stopping signal by the processor, the processor of the ophthalmic surgery foot pedal device, executing instructions contained in the non-transitory computer-readable medium, can send a force feedback signal to the force feedback mechanism of the foot pedal device to apply a stopping force. Another example of a stopping signal is laser mode ON with energy set too high In some implementations, the foot pedal device can be configured so that the stopping force has a value that is selectable for a specific operator. Accordingly, the non-transitory computer-readable medium may contain instructions executable by the processor to send a stopping signal that causes the force feedback mechanism to apply a stopping force of a specific value for a specific operator, wherein the operator is not able to overcome the stopping force by applying increased depression force to the movable member, at least not by using a normal or typical range of possible increased depression force applied to the foot pedal device.

Alternatively, the trigger signal can be a slowing signal indicating a present "slowing value". Accordingly, upon detecting a slowing value, the processor, executing instructions contained in the non-transitory computer-readable medium, can receive a slowing signal from the surgical console. The term "slowing signal" as used herein refers to a signal sent in response to a detection of a surgical parameter value indicating a present condition or a change in conditions in a parameter detected by the surgical console wherein the present surgery parameter value does not include a threshold surgical parameter.

The ophthalmic surgery foot pedal device is configured so that the slowing signal initiates the application of a slowing force to the movable member, wherein the term "slowing force" refers to a resistance force that does not prevent further depression of the movable member, but instead provides an increased resistance to depression of the movable member. Accordingly, following application of the slowing force to the movable member, further rotational movement of the movable member towards the closed position may be possible upon application of an increased depression force.

For example, in one implementation of the foot pedal device, the slowing signal may indicate that a present value (a "slowing value") of an ophthalmic surgery parameter is selected from a) between a maximum threshold value of the surgical parameter (a "stopping value") and a value at a set difference lower that the maximum threshold value of the surgical parameter, or b) between a minimum threshold value of the surgical parameter (a "stopping value") and a value at a set difference higher than the minimum threshold value of the surgical parameter.

For example, in relation to TOP, a minimum threshold value of a surgical parameter value may be a set threshold value of pressure (e.g., in mmHg), and a set difference may be 2 mmHg higher than the minimum threshold value of the surgical parameter value. Accordingly, for example, the ophthalmic surgery foot pedal device described herein can apply a slowing force to the movable member upon detecting a present value of a surgical parameter within a set difference respectively greater or less than a minimum or maximum threshold value of a surgical parameter.

Thus, the slowing force applied to the movable member in response to the slowing signal provides force feedback to the operator to warn the operator as present conditions approach set threshold values of surgical parameters during surgery.

In general, upon application of the slowing force, the ophthalmic surgery foot pedal device is configured to provide the operator with force feedback to an operator's foot such that the operator is informed of a requirement to apply an increased depressive force to the movable member of the foot pedal device if the operator intends to deliberately depress the movable member further towards the closed position, thereby sending a movement signal to the processor, which, upon executing instructions contained in the non-transitory computer-readable medium, sends a control signal to the surgical console to initiate an actuated control of an ophthalmic surgery tool. Accordingly, upon receiving the force feedback, the operator can decide whether to apply an increased depression force to the movable member, or alternatively to decrease or stop application of the depression force to the movable member.

In another implementation of the foot pedal device, the slowing signal can indicate that a present action of a surgical tool is non-optimal with respect to a present condition of the surgery, wherein the slowing signal indicates that a value of a parameter of the actuation of the surgical tool may be changed to improve performance of the surgery. For instance, the slowing signal can indicate that the value of the present motive power provided by the surgical console to promote a present action of an ophthalmic surgical tool is insufficient to effectively execute the controllable action of the ophthalmic surgical tool (a "slowing value"). Therefore, the slowing signal may indicate a selectable present value that is a product of present values of two or more ophthalmic surgery parameters. In particular, at least one of the ophthalmic surgery parameters may be a parameter of a controllable action of the ophthalmic surgery tool.

For example, in cataract surgery, a surgical console can be configured to provide a range of power output to a phacoemulsification tool, whereby an increase in power increases a lens cutting power of the phacoemulsification tool. A surgical parameter sensor can be configured, for example, to detect a surgical parameter of fluidics resistance, lens hardness and/or a phacoemulsification needle frequency parameter during phacoemulsification.

As would be understood by skilled persons, the action of phaco tips is analogous to that of combined 'chisels' and 'straws' that carve and aspirate lens material. An ultrasound generating mechanism of the phaco handpiece causes the tip attached to it to vibrate rapidly back and forth. The terms "tip excursion" or "stroke length" refer to the distance the tip displaces in the longitudinal direction at maximum power. Stroke length varies for different machines and typically ranges from 1.5-3.75 milli-inches. Phacoemulsification consoles typically allow the operator to alter phaco power and this is usually indicated as a percentage. Whenever the phaco power is set at 100 percent the stroke length is the maximum permissible for that machine. When the power is decreased by a given percentage, the stroke length also decreases. The frequency of a given handpiece is usually indicated in kilohertz (KHz). The frequency used most commonly is 40 KHz. Phaco needle movement creates mechanical power. Total power is a combination of the frequency of the needle movement and stroke length of the needle movement. This length is generally 0.002-0.006 inches. Most machines operate in the 0.002-0.004 inches range. Longer stroke lengths are prone to generate excess heat. The longer the stroke length, the greater the physical impact on the nucleus, and the greater the generation of cavitation forces. Phacoemulsification needles typically move at a frequency of between 35,000 to 45,000 cycles per second (Hz), and this frequency range is typically efficient for nuclear emulsification, whereas lower frequencies are less efficient and higher frequencies can generate excess heat.

Accordingly, the non-transitory computer-readable medium may contain a lookup table containing a range of optimal values of the controllable action of a surgical tool in view of present conditions of the surgery, for example values of parameters of two or more ophthalmic surgery parameters, wherein at least one of the ophthalmic surgery parameters may be a parameter of a controllable action of the ophthalmic surgery tool. In the foot pedal device, the processor, upon execution of a fourth set of instructions contained in the non-transitory computer readable medium, may be configured to compare the present value of a parameter of the controllable action of the surgical tool in view of the present values of the two or more ophthalmic surgery parameters with the optimal value contained in the lookup table in view of the present values of the two or more ophthalmic surgery parameters and determine that the present value of the parameter of the controllable action of the surgical tool is different than the optimal value of the parameter of the controllable action of the surgical tool.

For example, in operation, the foot pedal device can be configured so that the non-transitory computer-readable medium contains instructions according to a predetermined set of values for, e.g., a lens hardness parameter and/or the phacoemulsification needle frequency parameter that allow the processor to send a slowing signal to the force feedback mechanism upon receiving a surgical parameter signal indicating the increased lens hardness in excess of what is able to be effectively cut by the present power provided to the phacoemulsification tool, initiating the application of a slowing force to the movable member. Accordingly, the slowing force provides the operator with force feedback to the operator's foot, indicating that an increase in power supply to the phacoemulsification tool is required to more effectively cut the lens. The operator is thereby informed of a requirement to apply an increased depressive force to the movable member of the foot pedal device if the operator intends to depress the movable member further towards the closed position, and thereby send a control signal to surgical console to initiate an associated controllable action of the surgical tool, such as providing increased power to the phacoemulsification tool. Accordingly, upon receiving the force feedback, the operator can decide whether to apply an increased depressive force to the movable member, or alternatively to decrease or cease application of the depressive force to the movable member.

Accordingly, upon receipt of a slowing signal by the processor, the non-transitory computer-readable medium of the ophthalmic surgery foot pedal device can contain instructions for the processor to send a slowing signal to the force feedback mechanism of the foot pedal device to apply a slowing force.

In some implementations, the foot pedal device can be configured so that the slowing force has a value that is selectable for a specific operator. Accordingly, the non-transitory computer-readable medium may contain instructions executable by the processor to send a slowing signal that causes the force feedback mechanism to apply a slowing force of a specific value for a specific operator, wherein the operator is able to overcome the slowing force by applying increased depression force to the movable member e.g. a selectable set slowing force value that is sufficient to provide force feedback to the operator, but not greater than may be overcome by an increased depression force in response to the force feedback.

The foot pedal device may be configured to initiate force feedback in response to one or more trigger signals. In particular, the processor, acting on instructions contained in the non-transitory computer-readable medium, may be configured to receive one or more trigger signals from one or more surgical parameter sensors coupled with the surgical console.

Optionally, in order to assist the operator to discern what a particular application of force feedback indicates, the foot pedal device can also be operatively connected with means for communicating additional information concomitant with the force feedback, such as an audible or visual alert to the operator, for example that indicates in response to what trigger signal the force feedback is being applied. For example, upon application of a stopping force, the processor, executing instructions contained in the non-transitory computer-readable medium, can also be configured to initiate an audible alarm to be presented to the operator, or a visual indication, e.g. illumination of a light, or an indication presented on a screen to the operator, indicating a particular present stopping value. Similarly, upon initiation of a slowing force, an audible alarm or a visual indication can be presented to the operator indicating, a particular present slowing value.

Optionally, the ophthalmic surgery foot pedal device 100 may also include a depression force sensor 121 configured to detect a depression force value applied to the movable member. In FIG. 1A and FIG. 1B, the depression force measured by the depression force sensor is depicted as a downward dashed arrow 122 inside the depression force sensor 121. Accordingly, the non-transitory computer-readable medium 110 may also contain a fifth set of instructions which, when executed by the processor 109, cause the processor 109 to receive from the depression force sensor 121 a depression force value signal.

As explained above, while a depression force sensor is described extensively, those with ordinary skill in the art having the benefit of the present disclosure will readily appreciate that a wide variety of sensors can be used to detect movement, rotation, position, depression, force, etc. imparted onto the movable member of a foot pedal. In some cases, the foot pedal utilizes an angular position sensor (such as a Hall effect or optical encoder) to provide a signal to the console with the signal conveying a value proportional to foot pedal depression angle. Likewise, a modified depression angle in response to a slowing force can be used to transmit a further control signal to the console. Accordingly, the ophthalmic surgery foot pedal device 100 can include a sensor for detecting the angular position of the movable member.

Any suitable means for detecting a depression force applied to the movable member that is identifiable by persons skilled in the art upon reading of the present disclosure can be used in the ophthalmic surgery foot pedal device. For example, the depression force sensor can be a load cell. The term "load cell" as used herein refers to an electronic device that may include a transducer configured to convert a force into an electrical signal. Various types of load cells include piezoelectric, hydraulic, pneumatic, and strain gauge, among others identifiable by skilled persons.

The depression force value can be a first depression force value or a modified depression force value. The term "first depression force value" as used herein refers to a value of the depression force applied to the movable member coincident with the initiation of the slowing force to the movable member. The term "modified depression force value" as used herein refers to a value of the depression force applied to the movable member after initiation of the slowing force to the movable member. In particular, the modified depression force value can be a depression force value applied by the operator to the movable member of the ophthalmic surgery foot pedal device in response to the slowing force. In operation, as described herein, upon receiving the force feedback, the operator can decide whether to sustain, increase, decrease, or cease the depression force applied to the movable member.

In particular, the foot pedal device is configured to determine whether an increased depression force is a deliberate increase of depression force applied by the operator, wherein the operator intends to overcome the slowing force.

Accordingly, the processor 109, executing the instructions contained in the non-transitory computer-readable medium 110, can be configured to determine that the modified depression force value is a set threshold difference higher than the first depression force value, and in response to the determination, allow the slowing force to be overcome, and thereby allow further depression of the movable member 103 by the operator. Upon further depression of the movable member 103, the processor 109 can transmit, to the surgical console 111, a control signal to initiate actuation of a controllable action of the surgical tool 112. Thus, the control signal transmitted to initiate the actuation of the action or modified action of the surgical tool indicates an intentional, deliberate increase in depression force applied to the movable member 103 by the operator in view of the slowing signal. As a corollary, the processor 109 of the foot pedal device 100 configured in this way can determine that a modified depression force value that is higher than the first depression force value but below the set threshold difference higher than the first depression force indicates an unintentional increase in depression force value applied to the movable member 103. In this case, the slowing force applied to the movable member 103 will not be overcome, and the processor 109 will not send a control signal to the surgical console 111 to initiate the action or modified action of the surgical tool 112.

An advantage of the foot pedal device configured in this way, for example, is that an involuntary or unintentional depression of the movable member by the operator that is below the set threshold difference higher will not initiate the actuation of a controllable action of the surgical tool. This configuration of the foot pedal device provides a further control feature of the foot pedal device that may, for example, increase patient safety during surgery.

In some implementations, upon receipt of a slowing signal by the processor, the non-transitory computer-readable medium of the ophthalmic surgery foot pedal device may contain instructions for the processor to send a force feedback signal to the force feedback mechanism to apply a slowing force having a value that is greater than the first depression force value but less than the modified depression force value that is a set threshold difference higher than the first depression force value.

In some implementations, for example, the set threshold difference higher can be higher than the first depression force value by about 25%, 50%, 75%, 100%, 150%, 200%, or 300% or more.

Optionally, the non-transitory computer-readable medium of the ophthalmic surgery foot pedal device can also contain a sixth set of instructions allowing the processor to determine that the modified depression force value is a threshold difference lower than the first depression force value; and in response to the determination, cause the force feedback mechanism to end the application of the slowing force to the movable member. For example, upon receiving the force feedback, the operator may decide to decrease depression force (e.g., by raising their foot) or cease depression force altogether (e.g., by removing their foot from the movable member), whereupon the movable member may passively return towards the open position according to the action of the spring return mechanism.

In some implementations, for example, the set threshold difference lower can be lower than the first depression force value by about 25%, 50%, 75%, 100%, 150%, 200%, or 300% or more.

The modified depression force value can be a set threshold difference higher or lower than the first depression force value that is selectable for a specific operator and/or for a specific action of a surgical tool and/or surgical parameter. Accordingly, the foot pedal device can be configured to be calibrated to a specific operator. For example, the foot pedal device can be calibrated by recording a set of calibration depression force values for a specific operator. A calibration protocol can be established to record calibration vales to the non-transitory computer readable medium. During calibration, the operator can perform a set of foot depressions to the movable member, for example in presence or in absence of a slowing force. For example, a foot depression applied in absence of a slowing force can be considered as a "baseline" foot depression, having a depression force value that is applied under normal operating conditions in absence of a slowing signal. In operation, upon initiation of a slowing force, the baseline depression force value that is applied to the movable member coincident with the initiation of the slowing force can be the first depression force value. During calibration, the value of the slowing force may be selected by the operator in order to provide a suitable level of slowing force feedback to the selected operator. A suitable level of slowing force feedback may have a force value that provides force feedback to the selected operator, wherein the slowing force has a value not greater than can be overcome by the selected operator by applying an intentional, deliberately increased depression force. It should be understood that during calibration, the slowing force applied to the movable member may be a "simulated" slowing force, wherein the simulated slowing force may be applied to the movable member by the force feedback mechanism in absence of a slowing signal from the surgical console, in order to mimic the force feedback relating to a slowing signal that would be applied to the movable member during operation. In particular, a modified depression force value that is a set threshold difference higher than a first depression force value can be recorded and labeled in the non-transitory computer-readable medium as a modified depression force value that is applied, in response to the slowing force, that corresponds to an intentional, deliberate application of an increased depression force value by the operator. Following calibration, in operational use of the foot pedal device, the modified depression force value that is labeled as corresponding to an intentional, deliberate depression force value may be selected as the set threshold difference higher than the first depression force value for the specific operator. Alternatively, during calibration, a modified depression force value that is a set threshold difference lower than a first depression force value can be recorded and labeled in the non-transitory computer-readable medium as a modified depression force value that is applied, in response to the slowing force that corresponds to an intentional, deliberately decreased depression force value by the operator. Following calibration, in operational use of the foot pedal device, the modified depression force value that is labeled as corresponding to an intentional, deliberately decreased depression force value may be selected as the set threshold difference lower than the first depression force value for the specific operator. The deliberately decreased depression force may have a depression force of zero, wherein the operator removes the foot from the movable member.

In the ophthalmic surgery foot pedal device of the disclosure, the first, second, third, fourth, fifth and sixth sets of instructions described herein may be combined in any combination in one or more sets.

The ophthalmic surgery foot pedal device of the disclosure also has a power supply 123 electrically connected to electronic components of the foot pedal device described herein. The power supply can include a battery and/or a system configured for electrically powering the foot pedal device from a reticulated electricity supply (such as mains power, e.g., from a wall socket).

In some configurations, the foot pedal device 100 can include a wireless charging system for wireless charging of the foot pedal device 100 during use. In particular, the foot pedal device 100 may in some configurations have a plurality of connected components for integrated functions related to a plurality of ophthalmic surgery tools and surgical parameter sensors, the accordingly the foot pedal device 100 may have increased power supply requirements to effectively perform these functions. In particular, the foot peal described herein can in some configurations have a wireless charging pad 124 configured to wirelessly electrically charge the foot pedal device 100 during use. The terms "wireless charging", "inductive charging" or "cordless charging" as used herein refers to the use of an electromagnetic field to transfer energy between two objects through electromagnetic induction. This is usually done with a charging station, or charging base, otherwise known as a "wireless charging pad". Electrical energy is sent through an inductive coupling to an electrical device, which can then use that energy to charge batteries or power the device. Induction chargers typically use an induction coil to create an alternating electromagnetic field from within a charging base, and a second induction coil in the portable device takes power from the electromagnetic field and converts it back into electric current to charge the battery. The two induction coils in proximity combine to form an electrical transformer. Wireless charging systems suitable for use with the ophthalmic surgery foot pedal device 100 described herein are identifiable by persons skilled in the art upon reading of the present disclosure. In particular, wireless charging pads and induction coils configured for use with the power supply in the foot pedal device 100 can be those compatible with the Qi standard established by the Wireless Power Consortium, as would be understood by persons skilled in the art.

Figure 2:
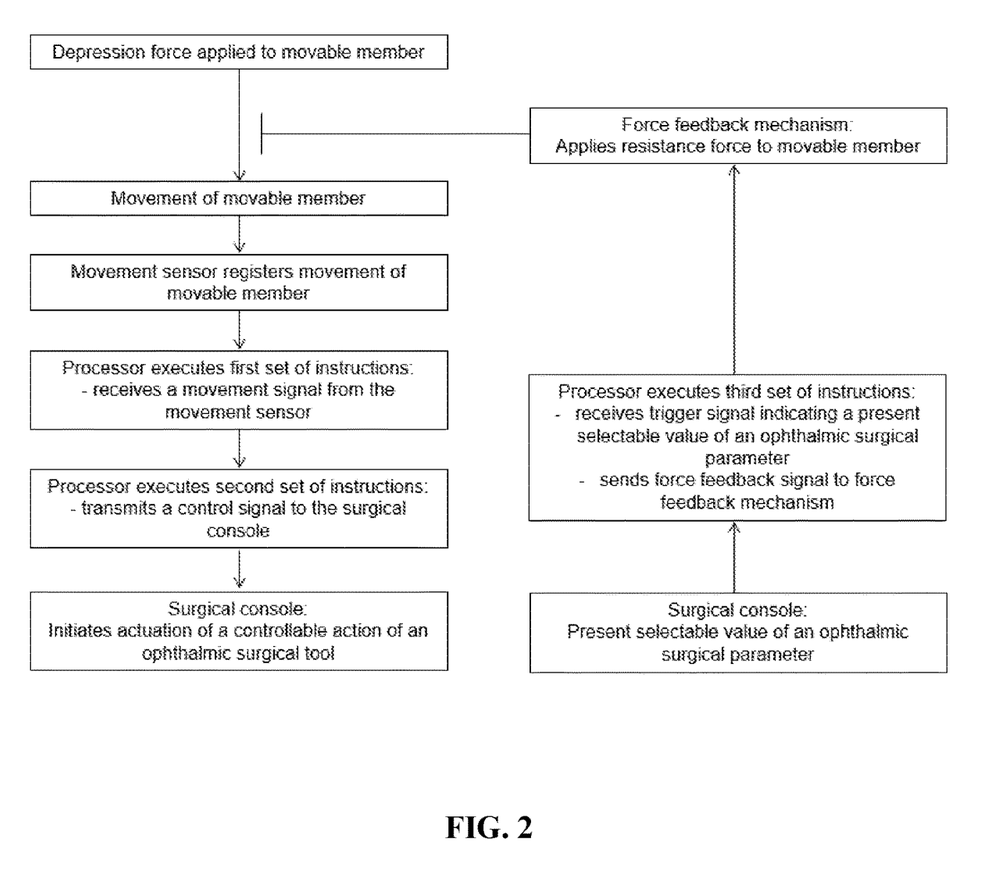
FIG. 2 shows an exemplary flow chart schematic illustrating a method of operation of the ophthalmic surgery foot pedal device.

A method of operation of the ophthalmic surgery foot pedal device is provided. FIG. 2 shows an exemplary flow chart schematic illustrating a method of operating the ophthalmic surgery foot pedal device described herein. The method includes the steps of: depressing the movable member, thereby causing movement of the movable member; executing, by the processor, a first set of instructions contained in the non-transitory computer-readable medium, causing the processor to receive a movement signal from the movement sensor indicating movement of the movable member; executing, by the processor, a second set of instructions contained in the non-transitory computer-readable medium, in response to the movement signal, causing the processor to transmit a control signal to a surgical console for initiating an actuation of an ophthalmic surgery tool coupled with the surgical console, wherein the ophthalmic surgical tool is configured to perform a controllable action that is actuated in response to a control signal; executing, by the processor, a third set of instructions contained in the non-transitory computer-readable medium, causing the processor to: receive a trigger signal from the surgical console, wherein the trigger signal indicates a present selectable value of an ophthalmic surgical parameter; and send a force feedback signal to the force feedback mechanism, in response to the trigger signal; and applying, by the force feedback mechanism, the resistance force to the movable member, upon receiving the force feedback signal. In FIG. 2, steps are shown in boxes and arrows are shown linking the steps. Lines having flat heads (rather than arrow heads) indicate blocking of the linkage between the indicated steps. As described herein, the resistance force may be either a slowing force or a stopping force.

Figure 3:
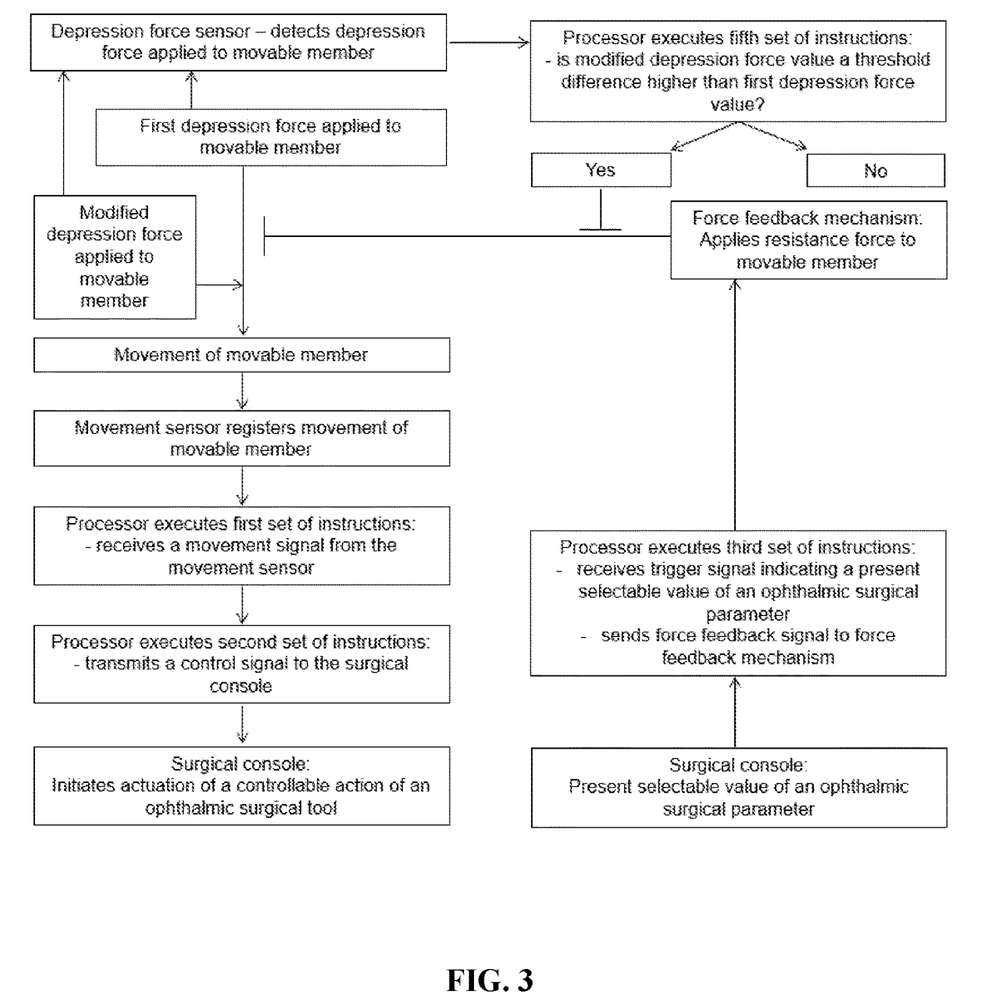
FIG. 3 shows another exemplary flow chart schematic illustrating a method of operation of the ophthalmic surgery foot pedal device.

FIG. 3 shows an additional an exemplary flow chart schematic illustrating a method of operating the ophthalmic surgery foot pedal device described herein. In particular, FIG. 3 illustrates that the method may further include executing, by the processor, a fifth set of instructions contained in the non-transitory computer-readable medium, causing the processor to: receive a first depression force value signal from the depression force sensor; receive a modified depression force value signal in response to the slowing force; make a determination that the modified depression force value is a threshold difference higher than the first depression force value; and transmit a control signal to the surgical console in response to the determination. In FIG. 3, steps are shown in boxes and arrows are shown linking the steps. Lines having flat heads (rather than arrow heads) indicate blocking of the linkage between the indicated steps.

Advantages of the ophthalmic foot pedal device of the disclosure include improved surgical suite integration, wherein the foot pedal device is responsive to present conditions of detectable surgical parameters, and allows integration of this information into the performance of actions using selected surgical tools. Accordingly, the foot pedal device of the disclosure provides the operator, such as an ophthalmic surgeon with advanced force feedback and allows more fine-tuned control of the surgery.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A foot pedal device for using during surgery, the foot pedal device comprising:
   a housing;
   a movable member;
   a movement sensor configured to register movement of the movable member;
   a processor;
   a non-transitory computer-readable medium;
   a force feedback mechanism configured to selectively apply a resistance force in opposition to a depression of the movable member; and
   a power supply configured to provide electrical power to the foot pedal device;
   wherein
   the non-transitory computer-readable medium contains a first set of instructions which, when executed by the processor, cause the processor to receive a movement signal from the movement sensor indicating movement of the movable member;
   the non-transitory computer-readable medium contains a second set of instructions which, when executed by the processor, cause the processor to transmit, in response to the movement signal, a control signal to a surgical console for initiating an actuation of a surgical tool coupled with the surgical console, wherein the surgical tool is configured to perform a controllable action that is actuated in response to a control signal;
   the non-transitory computer-readable medium contains a third set of instructions which, when executed by the processor, cause the processor to:
      receive, from the surgical console, a trigger signal indicating a present selectable value of a surgical parameter; and
      send, in response to the trigger signal, a force feedback signal to the force feedback mechanism;
   wherein the force feedback mechanism applies the resistance force to the movable member upon receiving the force feedback signal.

2. The foot pedal device of claim 1, wherein:
   the trigger signal is a stopping signal; indicating that the present value of a surgical parameter is selected from a) a value equal to or greater than a selectable maximum threshold value of the surgical parameter, and b) a value equal to or less than a minimum threshold value of the surgical parameter; and
   the resistance force is a stopping force that prevents depression of the movable member.

3. The foot pedal device of claim 1, wherein:
   the trigger signal is a slowing signal; and
   the resistance force is a slowing force providing a resistance to depression of the movable member, wherein the resistance does not prevent depression of the movable member.

4. The foot pedal device of claim 3, wherein the slowing signal indicates a present value of a surgical parameter that is selected from a) between a maximum threshold value of the surgical parameter and a value at a set difference lower that the maximum threshold value of the surgical parameter, or b) between a minimum threshold value of the surgical parameter and a value at a set difference higher than the minimum threshold value of the surgical parameter.

5. The foot pedal device of claim 3, wherein the slowing signal indicates a selectable present value that is a product of present values of two or more surgical parameters.

6. The foot pedal device of claim 5, wherein at least one of the surgical parameters is a parameter of a controllable action of the surgical tool.

7. The foot pedal device of claim 6, wherein the slowing signal indicates a present value of the parameter of the controllable action is a non-optimal value,
   wherein
   the non-transitory computer-readable medium further contains a lookup table containing a range of optimal values of the controllable action of a surgical tool in view of the two or more surgical parameters;
   the processor, upon execution of a fourth set of instructions contained in the non-transitory computer readable medium, is configured to compare the present value of a parameter of the controllable action of the surgical tool in view of the present values of the two or more surgical parameters with the optimal value contained in the lookup table in view of the present values of the two or more surgical parameters; and
   determine that the present value of the parameter of the controllable action of the surgical tool is different to the optimal value of the parameter of the controllable action of the surgical tool.

8. The foot pedal device of claim 1, wherein the surgical parameter is detectable by one or more surgical sensors coupled with the surgical console.

9. The foot pedal device of claim 8, wherein the surgical parameter sensor is configured to detect a surgical parameter selected from one of lens hardness, intra-ocular pressure, vacuum, fluidics resistance, irrigation pressure, irrigation valve speed, vent valve direction, vent speed, pump direction, pump speed, fluidics fluid level, infusion pressure, vitrectomy cutter cuts per minute (CPM), and laser power.

10. The foot pedal device of claim 1, wherein the surgical tool is selected from one of a flow pump, a vacuum pump, a phacoemulsification tool, a vitrectomy probe, a laser probe, a syringe, and an optical coherence tomography (OCT) imaging tool.

11. The foot pedal device of claim 1, wherein the controllable action is selected from one of stroke length, cutting speed, vacuum level, aspiration flow rate, irrigation valve speed, vent valve direction, vent speed, pump direction, pump speed; fluidics fluid level; infusion pressure; vitrectomy cutter cuts per minute (CPM), laser power, and syringe plunger depression.

12. The foot pedal device of claim 1, wherein the force feedback mechanism comprises at least one of a torque motor, a brushless torque motor, a frictional brake, an electromagnetic brake, and a pumping brake.

13. The foot pedal device of claim 1, further comprising:
   a depression force sensor configured to detect a depression force applied to the movable member,
   wherein the non-transitory computer-readable medium contains a fifth set of instructions which, when executed by the processor, cause the processor to:
   receive, from the depression force sensor, a first depression force value signal;

receive, from the depression force sensor, a modified depression force value signal in response to the slowing force;

make a determination that the modified depression force value is a threshold difference higher than the first depression force value; and in response to the determination, transmit a control signal to the surgical console.

14. The foot pedal device of claim 1, further comprising:
a depression force sensor configured to detect a depression force value applied to the movable member, wherein the non-transitory computer-readable medium contains a sixth set of instructions which, when executed by the processor, cause the processor to:

receive, from the depression force sensor, a first depression force value;

receive, from the depression force sensor, a modified depression force value in response to the slowing force;

determine that the modified depression force value is a threshold difference lower than the first depression force value; and in response, cause the force feedback mechanism to end the application of the slowing force.

15. The foot pedal device of claim 13 or 14, wherein the threshold difference is calibrated for a selected operator.

16. The foot pedal device of claim 15, wherein the threshold difference calibrated for a selected operator comprises recording a set of calibration depression force values for the selected operator, comprising:

performing a first foot depression to the movable member coincident with an initiation of a slowing force, wherein the first foot depression has a first depression force value;

recording the first depression force value to the non-transitory computer-readable medium;

performing a second foot depression to the movable member, wherein the second foot depression is a modified foot depression intentionally applied to the movable member in response to the slowing force to further depress the movable member; and the modified foot depression has a modified depression force value that is a threshold difference higher than the first depression force value; and recording the modified depression force value to the non-transitory computer-readable medium;

thereby recording a set of calibration depression force values for the selected operator.

17. The foot pedal device of claim 15, wherein the threshold difference calibrated for a selected operator comprises recording a set of calibration depression force values for the selected operator, comprising:

performing a first foot depression to the movable member coincident with an initiation of a slowing force, wherein the first foot depression has a first depression force value;

recording the first depression force value to the non-transitory computer-readable medium;

performing a second foot depression to the movable member, wherein the second foot depression is a modified foot depression applied to intentionally decrease or cease the depression force applied to the movable member in response to the slowing force; and the modified foot depression has a modified depression force value that is a threshold difference lower than the first depression force value; and recording the modified depression force value to the non-transitory computer-readable medium;

thereby recording a set of calibration depression force values for the selected operator.

18. The foot pedal device of claim 1, wherein the power supply further comprising a wireless charging system.

19. The foot pedal device of claim 1, wherein the force feedback mechanism comprises a brushless torque motor.

20. A method of operation of a foot pedal device, wherein the foot pedal device comprises:

a housing;

a movable member;

a movement sensor configured to register movement of the movable member;

a processor;

a non-transitory computer-readable medium;

a force feedback mechanism configured to selectively apply a resistance force in opposition to a depression of the movable member; and a power supply configured to provide electrical power to the foot pedal device;

the method comprising:

depressing the movable member, thereby causing movement of the movable member;

executing, by the processor, a first set of instructions contained in the non-transitory computer-readable medium, causing the processor to receive a movement signal from the movement sensor indicating movement of the movable member;

executing, by the processor, a second set of instructions contained in the non-transitory computer-readable medium, in response to the movement signal, causing the processor to transmit a control signal to a surgical console for initiating an actuation of a surgical tool coupled with the surgical console, wherein the surgical tool is configured to perform a controllable action that is actuated in response to a control signal;

executing, by the processor, a third set of instructions contained in the non-transitory computer-readable medium, causing the processor to:

receive a trigger signal from the surgical console, wherein the trigger signal indicates a present selectable value of a surgical parameter; and send a force feedback signal to the force feedback mechanism, in response to the trigger signal; and applying, by the force feedback mechanism, the resistance force to the movable member, upon receiving the force feedback signal.

21. The method of claim 20, wherein the foot pedal device further comprises a depression force sensor configured to detect a depression force applied to the movable member, the method comprising:

executing, by the processor, a fifth set of instructions contained in the non-transitory computer-readable medium, causing the processor to:

receive a first depression force value signal from the depression force sensor;

receive a modified depression force value signal in response to the slowing force;

make a determination that the modified depression force value is a threshold difference higher than the first depression force value; and transmit a control signal to the surgical console in response to the determination.

* * * * *